(12) United States Patent
Kieser

(10) Patent No.: US 9,424,503 B2
(45) Date of Patent: Aug. 23, 2016

(54) STRUCTURALLY ENCODED COMPONENT AND METHOD OF MANUFACTURING STRUCTURALLY ENCODED COMPONENT

(71) Applicant: Brian Kieser, San Antonio, TX (US)

(72) Inventor: Brian Kieser, San Antonio, TX (US)

(*) Notice: Subject to any disclaimer, the term of this patent is extended or adjusted under 35 U.S.C. 154(b) by 0 days.

(21) Appl. No.: 14/823,234

(22) Filed: Aug. 11, 2015

(65) Prior Publication Data

US 2016/0042261 A1 Feb. 11, 2016

Related U.S. Application Data

(60) Provisional application No. 62/035,875, filed on Aug. 11, 2014.

(51) Int. Cl.
*G06K 21/00* (2006.01)
*G06K 19/06* (2006.01)

(52) U.S. Cl.
CPC .... *G06K 19/06046* (2013.01); *G06K 19/06028* (2013.01); *G06K 19/06037* (2013.01); *G06K 19/06075* (2013.01); *G06K 19/06121* (2013.01)

(58) Field of Classification Search
USPC .............. 235/457, 462.01, 489, 491
See application file for complete search history.

(56) References Cited

U.S. PATENT DOCUMENTS

| | | | |
|---|---|---|---|
| 5,201,715 A | 4/1993 | Masters | |
| 5,726,433 A * | 3/1998 | Peng ................. | G06K 7/10693 235/462.36 |
| 5,977,431 A | 11/1999 | Knapp et al. | |
| 6,366,696 B1 | 4/2002 | Hertz et al. | |
| 7,028,375 B1 * | 4/2006 | Schaefer ................ | B25G 3/00 15/145 |
| 7,474,223 B2 | 1/2009 | Nycz et al. | |
| 7,650,888 B2 | 1/2010 | Maschke | |
| 7,855,812 B2 | 12/2010 | Gelsomini et al. | |
| 7,901,945 B2 | 3/2011 | Meiring et al. | |
| 8,114,063 B2 | 2/2012 | Sacco et al. | |
| 8,175,412 B2 | 5/2012 | Basri et al. | |
| 8,511,316 B2 | 8/2013 | Boese et al. | |
| 9,251,393 B2 * | 2/2016 | Pollack ................. | G01N 35/04 |
| 2001/0037220 A1 | 11/2001 | Merry et al. | |
| 2001/0049544 A1 | 12/2001 | Lee | |
| 2003/0003220 A1 | 1/2003 | Zhong et al. | |
| 2003/0047616 A1 * | 3/2003 | Mase ..................... | G06K 1/126 235/494 |
| 2004/0167637 A1 | 8/2004 | Biscup | |
| 2005/0237577 A1 | 10/2005 | Alasia et al. | |
| 2005/0282291 A1 * | 12/2005 | Pankratz ............ | G01N 35/1016 436/180 |

(Continued)

FOREIGN PATENT DOCUMENTS

WO WO2005065596 A1 7/2005

OTHER PUBLICATIONS

International Search Report and Written Opinion of the International Searching Authority, PCT/US2015/015383, Kieser, Apr. 29, 2015.

(Continued)

*Primary Examiner* — Tuyen K Vo
(74) *Attorney, Agent, or Firm* — Ice Miller LLP

(57) ABSTRACT

A structurally encoded component stores identification data and comprises a readable body. The readable body comprises at least one detectable element and indicia as a plurality of detectable elements disposed within the structurally encoded component. The indicia are discernible by at least one of x-ray, fluoroscopy, computed tomography, electromagnetic radiation, ultrasound, positron emission tomography, and magnetic resonance imaging.

36 Claims, 14 Drawing Sheets

(56) References Cited

U.S. PATENT DOCUMENTS

| | | | |
|---|---|---|---|
| 2006/0097512 A1* | 5/2006 | Isherwood | D21H 21/42 283/72 |
| 2006/0212096 A1 | 9/2006 | Stevenson | |
| 2006/0235488 A1 | 10/2006 | Nycz et al. | |
| 2006/0247847 A1* | 11/2006 | Carter | A47F 10/04 701/498 |
| 2006/0282168 A1 | 12/2006 | Sherman et al. | |
| 2007/0043429 A1 | 2/2007 | Hegel et al. | |
| 2007/0239481 A1 | 10/2007 | Disilvestro et al. | |
| 2008/0048855 A1 | 2/2008 | Berger | |
| 2008/0201007 A1 | 8/2008 | Boyden et al. | |
| 2008/0230421 A1 | 9/2008 | Pleil et al. | |
| 2008/0230422 A1 | 9/2008 | Pleil et al. | |
| 2008/0255425 A1 | 10/2008 | Voegele et al. | |
| 2008/0255537 A1 | 10/2008 | Voegele et al. | |
| 2009/0087911 A1* | 4/2009 | Ramos | E21B 47/1015 436/27 |
| 2009/0198306 A1 | 8/2009 | Goetz et al. | |
| 2009/0218401 A1* | 9/2009 | Moran | G06K 5/00 235/439 |
| 2009/0250512 A1 | 10/2009 | Deck et al. | |
| 2009/0306742 A1 | 12/2009 | Van Dijk et al. | |
| 2010/0080426 A1 | 4/2010 | Schmitt et al. | |
| 2010/0131023 A1 | 5/2010 | Costello et al. | |
| 2010/0168763 A1 | 7/2010 | Zhao et al. | |
| 2010/0198057 A1 | 8/2010 | Kerr et al. | |
| 2011/0004094 A1 | 1/2011 | Stubbs et al. | |
| 2011/0047135 A1 | 2/2011 | Vizethann et al. | |
| 2011/0074629 A1* | 3/2011 | Khan | G01S 19/14 342/357.64 |
| 2011/0084241 A1* | 4/2011 | Garden | C08L 63/00 252/588 |
| 2011/0093619 A1 | 4/2011 | Nelson | |
| 2011/0125253 A1 | 5/2011 | Casanova et al. | |
| 2011/0160558 A1 | 6/2011 | Rassatt et al. | |
| 2011/0270082 A1 | 11/2011 | Turner et al. | |
| 2012/0071735 A1 | 3/2012 | Caylor et al. | |
| 2012/0271248 A1 | 10/2012 | Nesbitt et al. | |
| 2012/0292814 A1 | 11/2012 | Spratt et al. | |
| 2013/0053680 A1 | 2/2013 | Frey | |
| 2013/0110248 A1 | 5/2013 | Zipnick | |
| 2013/0236874 A1 | 9/2013 | Iannotti et al. | |

OTHER PUBLICATIONS

International Search Report and Written Opinion of the International Searching Authority, PCT/US2015/015366, Kieser, Jun. 22, 2015.
International Search Report and Written Opinion of the International Searching Authority, PCT/US2015/015345, Kieser, Jan. 22, 2016.
Groeger "FDA lacks system for tracking medical devices that malfunction," Denver Post, May 4, 2012, 2 pages (found at http://www.denverpost.com/nationworld/ci_20544821/fda-lacks-system-tracking-medical-devices-that-malfunction).
International Search Report and Written Opinion for International (PCT) Patent Application No. PCT/US2012/052016, mailed Nov. 16, 2012, Applicant: Frey, George 8 pages.

\* cited by examiner

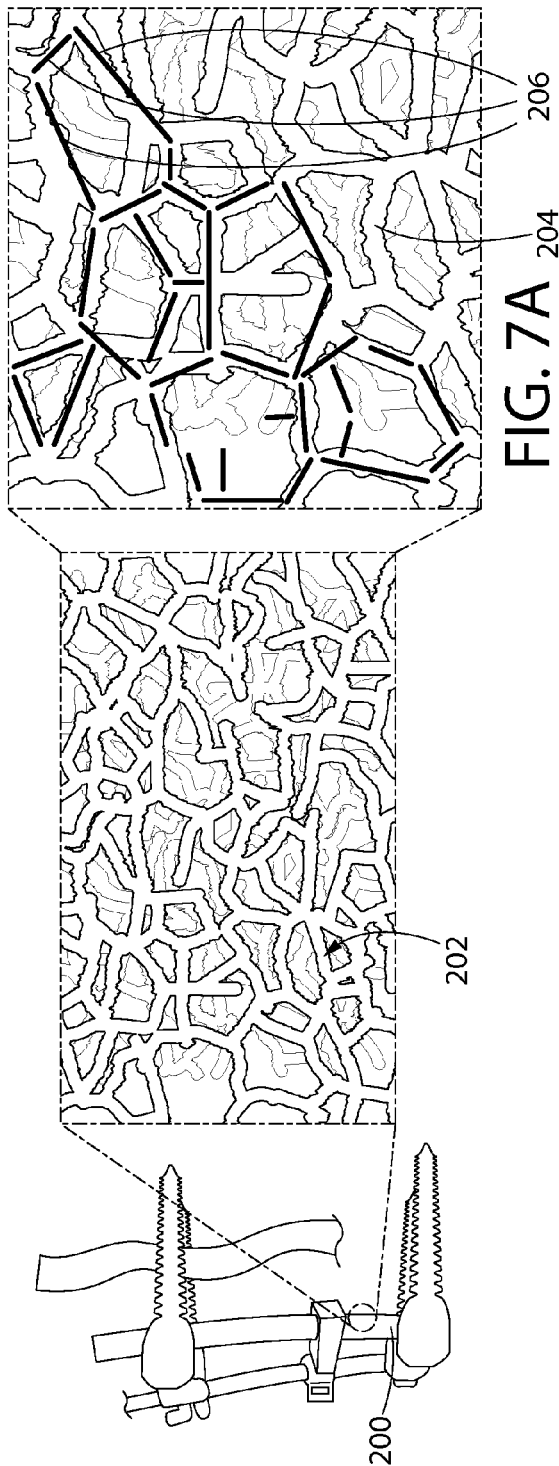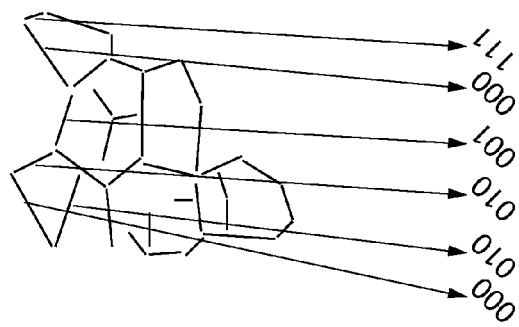
FIG. 7A
FIG. 8A

_US 9,424,503 B2_

STRUCTURALLY ENCODED COMPONENT AND METHOD OF MANUFACTURING STRUCTURALLY ENCODED COMPONENT

FIELD OF THE INVENTION

The present disclosure relates to structurally encoding objects and, in particular, to structurally encoded components.

BACKGROUND OF THE INVENTION

The security and identification of particular goods, parts, or components may require an identification tag, plate, or label in the form of a series of numbers or letters, a barcode, or another type of readable code. Such identification means may become ineffective due to wear, intentional or unintentional removal, or another type of alteration. For effective tracking, identification, and updates, component data storage and communication means must be more robust than what is currently available for sensitive objects, such as medical devices and implants, vehicles or vehicle parts, aircraft or aircraft parts, spacecraft or spacecraft parts, military equipment, firearms or other weapons, jewelry or similar valuables, commercial electronic devices, toys and other commercial goods, or pharmaceutical goods, as disclosed in U.S. Pat. No. 7,900,832, which is hereby incorporated herein by reference. Moreover, the size of existing identification devices limits the amount of information capable of being included in the data storage and communication means.

SUMMARY OF THE INVENTION

In accordance with an aspect of the invention, a structurally encoded component is provided comprising an outer structure portion of the structurally encoded component and a readable portion of the structurally encoded component. The readable portion may comprise a readable or radio-reflective element, such as a radiopaque element, and indicia disposed on at least one surface thereof or disposed within the structurally encoded component. The indicia may include a plurality of modifications to at least one surface of the readable portion or a plurality of elements disposed within the readable portion such that the indicia are discernible by any imaging modality, such as at least one of x-ray, fluoroscopy, computed tomography, electromagnetic radiation, ultrasound, positron emission tomography, and magnetic resonance imaging. The invention likewise may be applied advantageously in industrial imaging methods, modalities, and protocols, such as for inspection, quality control, inventory management, anti-counterfeiting, and other similar purposes.

In accordance with further aspects of the invention, the readable portion may be integral with the main portion. The readable portion may also be disposed upon the main portion. The plurality of modifications may include an array of holes in the at least one surface of the readable element. The plurality of modifications may include an array of notches or variations of density in the at least one surface of the readable portion. The array of notches in the at least one surface of the readable portion may form at least one bar code. The at least one bar code may comprise an error correction and/or detection code, such as a Hamming code. The plurality of modifications may be less than or equal to two centimeters in length.

In accordance with further aspects of the invention, a system for identifying a structurally encoded component is provided comprising an outer structure portion and a readable portion. The readable portion may comprise a readable element and indicia disposed on at least one surface thereof. The indicia may include a plurality of modifications to at least one surface of the readable portion or a plurality of elements disposed within the readable portion. The indicia may further include a database containing a plurality of records associated with a plurality of structurally encoded components and a user interface comprising means for displaying information associated with the indicia based on the plurality of records. The indicia may be discernible by at least one of x-ray, fluoroscopy, computed tomography, electromagnetic radiation, ultrasound, positron emission tomography, and magnetic resonance imaging.

The plurality of modifications may include an array of holes in the at least one surface of the readable portion. The plurality of modifications may include an array of notches in the at least one surface of the readable portion. The array of notches in the at least one surface of the readable portion may form at least one bar code. The at least one bar code may comprise an error correction and/or detection code, such as a Hamming code.

In accordance with further aspects of the invention, a method of identifying a micromanufactured structurally encoded component is provided comprising discerning indicia by at least one of x-ray, fluoroscopy, computed tomography, electromagnetic radiation, ultrasound, positron emission tomography, and magnetic resonance imaging. The indicia may include a plurality of modifications to at least one surface of a readable portion or a plurality of elements disposed within a readable portion. The method of identifying a micromanufactured structurally encoded component may further comprise accessing a plurality of records associated with at least one of a plurality of structurally encoded components and providing information associated with the micromanufactured structurally encoded component based on the indicia and the plurality of records. As used herein, the term "micromanufactured" encompasses all microfabrication techniques such as additive manufacturing and micromachining, and use of this term is not intended to limit the size or scale constraints or the type of the manufacturing process in any way. The term is used to elucidate the desire for the readable portion or the detectable portion of the structurally encoded component of the present disclosure to be either an incorporated portion of a structurally encoded component or of a size capable of being coupled to, assembled with, or attached to a separate component or in a larger assembly.

In accordance with further aspects of the invention, the method of identifying a micromanufactured structurally encoded component may further comprise displaying information associated with the micromanufactured structurally encoded component based on the indicia and the plurality of records through a user interface. The readable portion may be disposed upon an outer structure portion of the micromanufactured structurally encoded component. The plurality of modifications may include an array of holes in the at least one surface of the readable portion. The plurality of modifications may include an array of notches in the at least one surface of the readable portion. The array of notches in the at least one surface of the readable portion may form at least one bar code. The at least one bar code may comprise a Hamming code or other similar methods for error detection and/or correction that are known in the coding theory art. Additionally, data compression may be used in the coded indicia of an embodiment.

In accordance with further aspects of the invention, a structurally encoded component is provided comprising an outer structure portion of the structurally encoded component and a readable portion of the structurally encoded component. The readable portion may comprise a plurality of laminae or laminar planes (a finite planar volume). The plurality of laminae or laminar planes may correspond to physical surfaces, edges, or structures, or may be imaginary. A structurally encoded component may be divided into the plurality of laminae or laminar planes, actual or imaginary, and the plurality of laminae or laminar planes may be oriented in any direction relative to the component. Each of the laminae, hereafter referred to as "laminar planes," may comprise separately readable indicia such that the indicia may be discernible in three dimensions by at least one of x-ray, fluoroscopy, computed tomography, electromagnetic radiation, ultrasound, positron emission tomography, and magnetic resonance imaging.

The readable portion may be integral with the main portion. Also, the readable portion may be disposed upon the main portion. Further, the indicia may include an array of voids on or in a corresponding laminar plane of the readable portion. The indicia may include an array of embedded markers on or in a corresponding laminar plane of the readable portion. The embedded markers may comprise a modulation of material compositions such that a first material composition of at least one first embedded marker is different than a second material composition of at least one second embedded marker. Further, the indicia may include a first array of embedded markers on or in a first laminar plane of the readable portion and a second array of embedded markers on or in a second laminar plane of the readable portion. The first array may comprise a first embedded marker having a first material composition different than a second material composition of a second embedded marker disposed in the second array. The indicia may comprise information in the form of a code. The code may comprise a Hamming code or other similar methods for error detection and/or correction that are known in the coding theory art. Additionally, data compression may be used in the coded indicia of an embodiment.

In accordance with further aspects of the present disclosure, a method of manufacturing an identifiable structurally encoded component is provided comprising providing an outer structure portion of the structurally encoded component, providing a readable portion of the identifiable structurally encoded component, printing a first material onto a first readable portion surface to create a first printed layer, and printing the first material onto the first printed layer to create a second printed layer. The printing of the first material onto the first readable portion surface or the printing of the first material onto the first printed layer may comprise printing encoded indicia. The encoded indicia may comprise voids in the first material or measurable variations in density. The method of manufacturing an identifiable structurally encoded component may further comprise printing a second material onto at least one of the first readable portion surface and the first printed layer, such that the encoded indicia comprises the second material.

In accordance with further aspects of the present disclosure, a structurally encoded component is provided comprising an outer structure portion of the structurally encoded component and a readable portion of the structurally encoded component. The readable portion comprises an internal structure inside the readable portion. The internal structure comprises a plurality of linking structures. Each of the linking structures has a predetermined size or orientation. The linking structures are interconnected to substantially form the internal structure. The linking structures form predetermined indicia such that the indicia are discernible by x-ray, fluoroscopy, computed tomography, electromagnetic radiation, ultrasound, positron emission tomography, and/or magnetic resonance imaging. The readable portion may be integral with the main portion or disposed upon the main portion. The indicia in the readable portion of the structurally encoded component may comprise a Hamming code or other similar methods for error detection and/or correction that are known in the coding theory art. Additionally, data compression may be used in the coded indicia of an embodiment.

BRIEF DESCRIPTION OF THE FIGURES

While the specification concludes with claims particularly pointing out and distinctly claiming the present disclosure, it is believed that the present disclosure will be better understood from the following description in conjunction with the accompanying Drawing Figures, in which like reference numerals identify like elements, and wherein:

FIG. 7A is an enlarged cross sectional view of a structurally encoded component in accordance with further aspects of the present disclosure;

FIG. 8A is a diagram relating to indicia data of a structurally encoded component in accordance with further aspects of the present disclosure;

DETAILED DESCRIPTION

In the following detailed description of an embodiment, reference is made to the accompanying drawings that form a part hereof, and in which is shown by way of illustration, and not by way of limitation, a specific embodiment in which the present disclosure may be practiced. It is to be understood that other embodiments may be utilized and that changes may be made without departing from the spirit and scope of the present disclosure.

The present disclosure relates to U.S. provisional patent application 61/938,475, U.S. patent application Ser. No. 14/302,133, U.S. patent application Ser. No. 14/302,171, and U.S. patent application Ser. No. 14/302,197, all of which are hereby incorporated by reference in their entirety.

Figure 1:
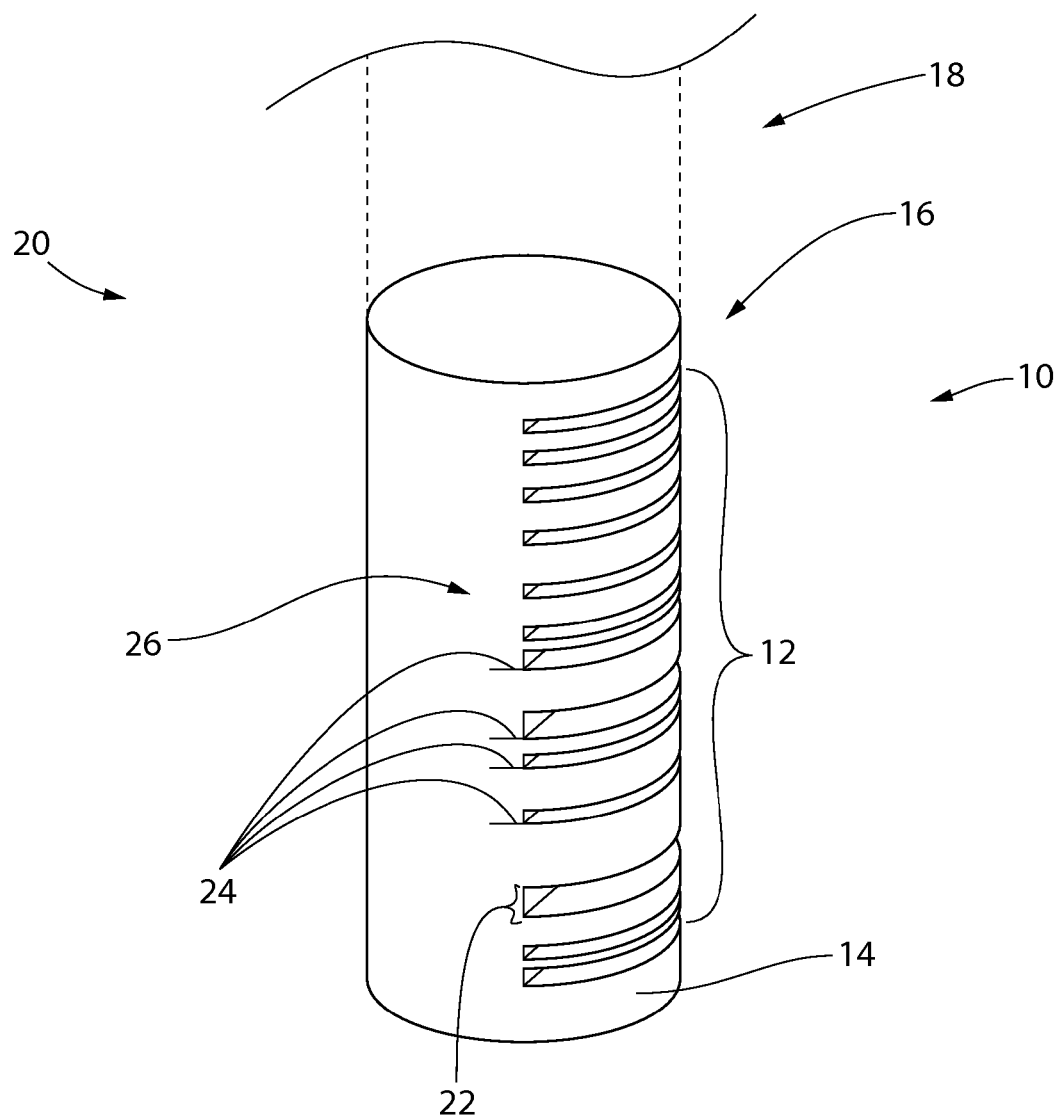
FIG. 1 is a side perspective view of a structurally encoded component in accordance with aspects of the present disclosure.

Reference is now made to FIG. 1, which shows a structurally encoded component rod structure 10 having a series of notches 12 in one longitudinal side 14 of the rod structure 10. The structurally encoded component rod structure 10 of the embodiment of FIG. 1 features a readable portion 16 shown in FIG. 1 to be integral with an outer structure portion 18 of a structurally encoded component 20. The structural encoding may also be integrated within a component so as to require imaging methods to obtain the encoded data. One or more embodiments of the structurally encoded component 20 described in the present disclosure includes a readable portion 16 and/or indicia 26 disposed at a subsurface location of the structurally encoded component. In this way, one could prevent modification of the encoding so as to prevent counterfeiting of original equipment manufacturer (OEM) parts. Alternatively, the readable portion 16 of the structurally encoded component 20 may be disposed upon the main portion 18 of the structurally encoded component 20. As used herein, a structurally encoded component refers to any component, device, part, assembly, or other physical structure capable of being encoded. The present disclosure further includes unique device identification and information extraction through high data density structural encoding.

The readable portion, or any readable element, as discussed throughout the present disclosure, may be a radiopaque element or another structure with properties capable of being detected using such methods as x-ray, fluoroscopy, computed tomography, ultrasound, positron emission tomography, magnetic resonance imaging, other forms of imaging, including medical imaging and industrial imaging, known in the art, or any imaging device or system that utilizes one or more frequencies and/or wavelengths along the electromagnetic spectrum. The readable portion 16 may be coupled to the main portion 18 by such means as fasteners or adhesives or through interference fit. Each of the notches 12 is a modification to the surface of the readable portion 16, has a predetermined width 22, and is located at a predetermined axial position 24 so as to create indicia 26 representing one-dimensional data. The rod structure 10 in an embodiment is a radiopaque structure, such as a tantalum rod. As will be further described below, the rod structure 10 may have a variable density such that the rod structure contains indicia in the form of a variable density internal structure or a particular mesh structure created by additive manufacturing, thereby increasing the density of data coding. After fabricating the structurally encoded component, the rod structure 10 and indicia 26 are detectable and readable via a variety of methods such as x-ray, fluoroscopy, computed tomography, electromagnetic radiation, ultrasound, positron emission tomography, and magnetic resonance imaging. The indicia 26 is detected and received by conventional imaging devices. Imaging software, preferably high resolution imaging software, then reads the data from the indicia 26 to decode and store and/or display the information from the structurally encoded component 20.

In a first embodiment of the present disclosure, the data represented by the indicia 26 on the surface of the rod structure 10 references unique information located in an external database. One example of such information includes data from the indicia 26 representing a unique numerical identifier corresponding to a wealth of information located in an external database.

In further embodiments of the present information, the size of the indicia may be decreased, and the density of the data thereby increased, such that additional information beyond mere reference data may be recorded onto the structurally encoded component. Such embodiments are further discussed below.

In an embodiment of the present disclosure, error correction is used to increase the resolution of the imaging technology, thereby allowing an increase in data density. Error correction is discussed in more detail below.

Figure 9:
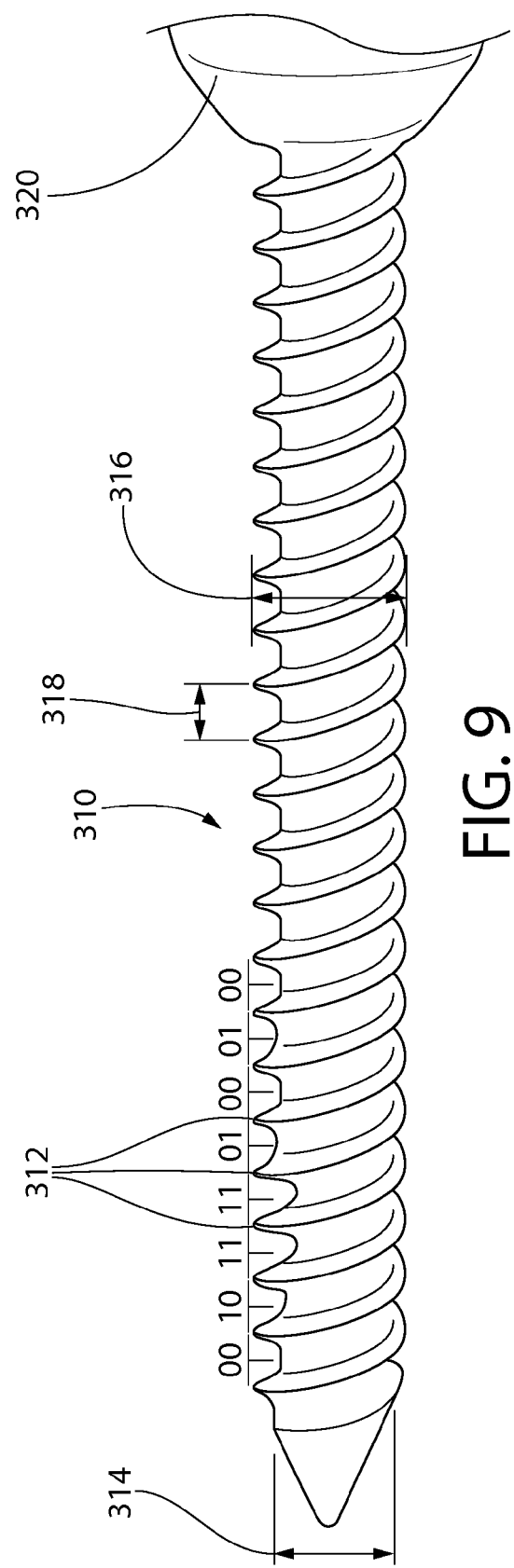
FIG. 9 is a side perspective view of a structurally encoded component in accordance with further aspects of the present disclosure.

Referring now to FIG. 9, rod structure 310 includes a plurality of threads 312 in a spiral or helical configuration around the circumference of the rod structure 310. Although the threads 312 shown in FIG. 9 are continuous to form a screw structure, such as a machine screw, the inner diameter 314 between adjacent threads 312 is varied to form indicia. As indicated in FIG. 9, the predetermined indicia allow coded data to appear within the functional structure of the rod structure 310 before and after structurally encoded component. Alternatively, the outer diameter 316 of threads 312 may be varied in addition to, or instead of, the variation of the inner diameter 314 to retain coded indicia on the rod structure 310. Further, the axial spacing 318 between adjacent threads 312 may be varied in order to store data. Even further, the particular shape of the spacing between adjacent threads 312, such as a square, triangular, or circular shape, may also allow data storage in the rod structure 310. A variation of this embodiment includes a micromanufactured structurally encoded component having indicia in or on the head 320 of the rod structure 310, such as coded indicia in the head of a machine screw.

Any of the embodiments, including each particular structure, disclosed in the present application may include structurally encoded components having the forms of, or being incorporated into, screws, rods, or other devices.

Figure 2:
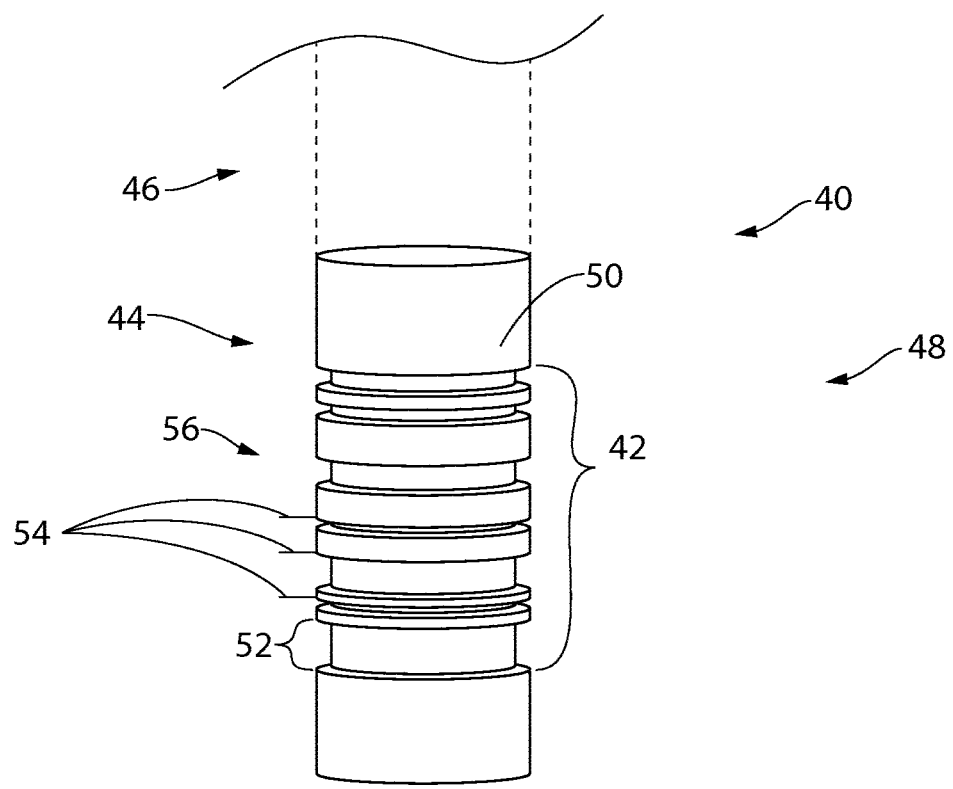
FIG. 2 is a side perspective view of a structurally encoded component in accordance with further aspects of the present disclosure.

Referring now to FIG. 2, a structurally encoded component rod structure 40 of an embodiment of the present disclosure features a series of notches 42 around the circumference of the rod structure 40. The structurally encoded component rod structure 40 of an embodiment of FIG. 2 features a readable portion 44 shown in FIG. 2 to be integral with an outer structure portion 46 of a structurally encoded component 48. Alternatively, the readable portion 44 of the structurally encoded component 48 may be disposed upon the main portion 46 of the structurally encoded component 48. The readable portion 44 may be coupled to the main portion 46 by such means as fasteners or adhesives or through interference fit. Each of the notches 42 is a modification to an exterior surface 50 of the readable portion 44, has a predetermined width 52, and is located at a predetermined axial position 54 so as to create indicia 56 representing one-dimensional data. The rod structure 40 in an embodiment is a radiopaque structure, such as a metallic rod. After integrating the structurally encoded component into or onto an assembly or separate structure, the rod structure 40 and indicia 56 are detectable and readable via a variety of imaging methods such as x-ray, fluoroscopy, computed tomography, electromagnetic radiation, ultrasound, positron emission tomography, and magnetic resonance imaging. The notches 42 of the embodiment may be created using known manufacturing methods, such as using a lathe, milling machine, wire electrical discharge machining (EDM) machine, or other machining techniques or through additive manufacturing processes, as further discussed below. As opposed to indicia located only on a side of a rod structure as shown in FIG. 1, positioning of indicia 56 around the circumference of the rod structure 40, as shown in FIG. 2, increases visibility of the indicia 56 and readability of the data by imaging methods. The indicia 56 is detected and received by imaging devices, which transmits the data to imaging software with sufficient resolution for accurately resolving the indicia. The imaging software reads the indicia 56 to decode and store and/or display the information from the structurally encoded component 48.

Although the indicia 26 and 56 shown in FIGS. 1 and 2 is oriented in a direction perpendicular to the axis of the rod structures 10 and 40, the indicia of the rod structures 10 and 40 may be oriented in a skewed or slanted orientation such that the indicia is not perpendicular to the axis of the rod structures 10 and 40. As will be recognized by one having ordinary skill in the art, any embodiment of the exemplary rod structures shown in FIGS. 1-3 and 9 may include notches, threads, or similar surface modification. Furthermore, each notch, thread, or similar structure may vary in depth, cross-section, or geometric shape across the series or array for further data storage.

In an embodiment of the present disclosure, the data represented by the indicia 56 on the surface of the rod structure references unique information located in an external database. One example of such information includes the data from the indicia 56 representing a unique number corresponding to a wealth of information located in an external database, such information including manufacturer, model, design file, batch, lot, date of manufacture, sales, supply chain, engineering, assembly, material(s), history, ownership, and/or manufacturing process data.

Error correction is used in an embodiment of the present disclosure to increase the resolution of the imaging technology, thereby allowing an increase in data density for a given measurement technology. By encoding, for example, a number into the structurally encoded component through micromachined holes and/or notches, sufficient permutations of the code can be recorded. In an embodiment of a structurally encoded component according to the present disclosure, a structurally encoded component contains, for one example, 400 micron discrete notches. The full code width and the bit count could, in this example, be dictated by machining precision and accuracy, number of variable machining widths (e.g., 100 microns, 200 microns, and 300 microns), total bar length, and image resolution. To ensure robustness in the encoding scheme, error correction in the form of a Hamming code is implemented in an embodiment but any error correction method known in the coding theory art could be employed. In the embodiment shown in FIGS. 1 and 2, four variable width notches every 250 microns allow eight bits of data to be encoded reliably every millimeter and read by a computed tomography scan with sufficient resolution to identify the notches. This is an example under an embodiment having values that are "power of 2 friendly" in order to clarify one embodiment of the present disclosure. The specific values of any particular embodiment of the present disclosure depend upon the imaging and manufacturing resolution, which will improve over time, as one having ordinary skill in the art may recognize.

Figure 3:
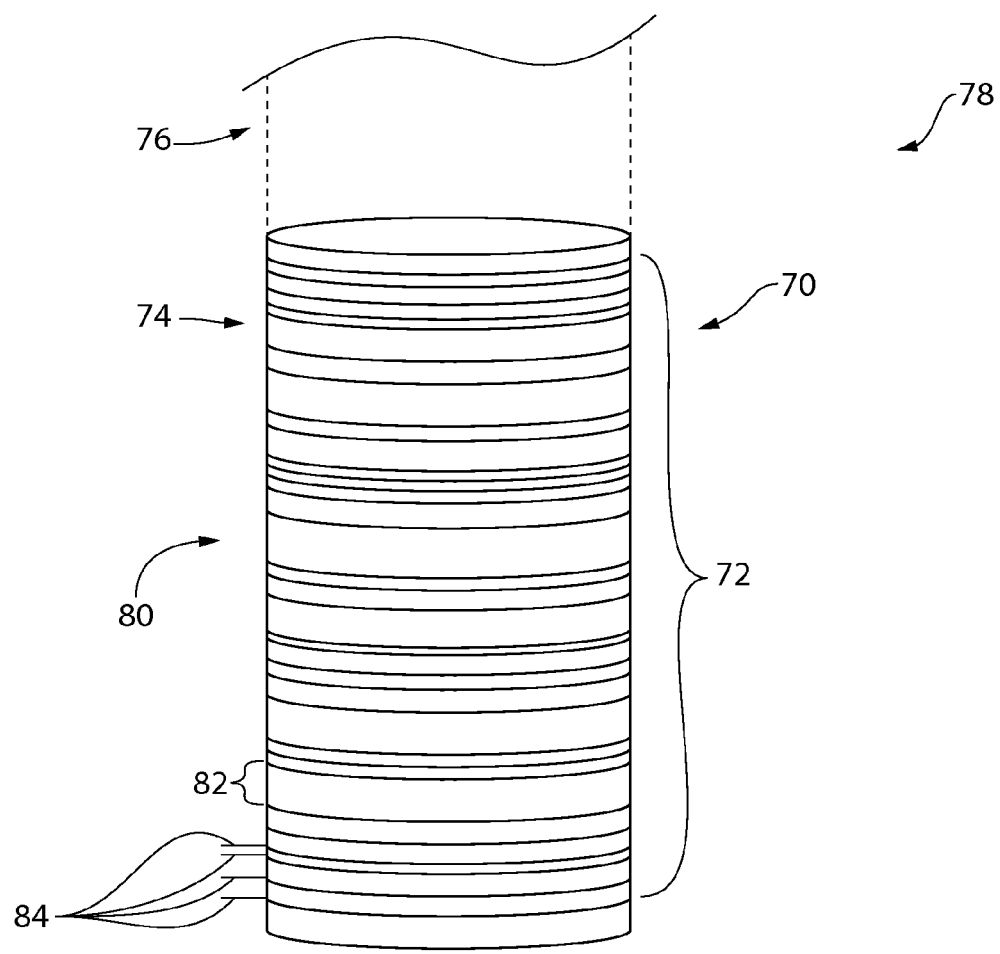
FIG. 3 is a side perspective view of a structurally encoded component in accordance with further aspects of the present disclosure.

Referring now to FIG. 3, a structurally encoded component rod structure 70 of an embodiment of the present disclosure features multiple materials in discrete layers 72 to create one-dimensional data around the circumference of the rod structure 70. The structurally encoded component rod structure 70 of the embodiment of FIG. 3 features a readable portion 74 shown in FIG. 3 to be integral with an outer structure portion 76 of a structurally encoded component 78.

Alternatively, the readable portion 74 of the structurally encoded component 78 may be disposed upon the main portion 76 of the structurally encoded component 78. The readable portion 74 may be coupled to the main portion 76 by such means as fasteners or adhesives or through interference fit. Similar to the notched indicia shown in FIGS. 1 and 2, the variance of material across the layers 72 in the embodiment shown in FIG. 3 creates indicia 80 representing data that is readable across the axial dimension of the rod structure 70. Alternative embodiments may feature multiple material layers readable across a different dimension or a structure having a different shape constructed using layers of multiple materials.

Referring again to an embodiment of FIG. 3, each of the distinct material layers 72 has a predetermined width 82 and is located at a predetermined axial position 84 so as to create the indicia 80 representing one-dimensional data. At least one of the layers 72 in the rod structure 70 of FIG. 3 may be a radiopaque structure. In an embodiment each of the layers 72 is composed of a particular material having some degree of opacity. Like the rod structures of FIGS. 1 and 2, after incorporation of the structurally encoded component into, onto, or with a separate assembly or component, the rod structure 70 and indicia 80 of the structurally encoded component 78 of FIG. 3 are detectable and readable via a variety of imaging methods such as x-ray, fluoroscopy, computed tomography, electromagnetic radiation, ultrasound, positron emission tomography, and magnetic resonance imaging. The indicia layers 72 of the embodiment shown in FIG. 3 are structured so as to be visible from any side of the rod structure 70 to increase readability of the data by imaging methods. The indicia 80 are detected and received by imaging devices, which transmits the data to imaging software, preferably high resolution imaging software. The imaging software reads the indicia 80 to decode and store and/or display the information from the structurally encoded component 78.

The information or data encoded onto or into the structurally encoded components of the embodiments disclosed in the present disclosure may be detected, decoded, read, transferred, stored, displayed, or processed according to such methods and devices disclosed in U.S. Pat. No. 8,233,967 or U.S. Patent Application Publication No. 2013/0053680, both of which are hereby incorporated herein by reference.

The structurally encoded component 78 of FIG. 3 is manufactured using additive manufacturing (AM) techniques. Due to their precision and programmability, AM processes may be used for any of the embodiments shown in FIGS. 1-3 to allow a reduction in the size of the indicia and, therefore, increased density of data included onto the surface of the structurally encoded component rod structure. In some cases, machining may be sufficient to provide the indicia necessary for the structurally encoded component rod structure. With increased data density, additional information beyond mere reference data may be recorded onto the structurally encoded component 78. The data recorded onto the structurally encoded component itself may include manufacturer, model, design file data, batch, lot, date of manufacture, sales, supply chain, engineering, assembly, material(s), component or assembly history, ownership, or manufacturing process data that would otherwise need to be stored in and accessed through an external database. Additionally, AM allows complex, mass customized, internal structures otherwise unavailable with conventional manufacturing, including three-dimensional structures discussed in further detail below. Moreover, AM eliminates the need for tooling and can therefore allow fabrication of structurally encoded components with unique identifiers within the structure with no additional masks, molds or user interaction.

ASTM International formed Committee F42 on Additive Manufacturing Technologies in 2009 with the mission of setting the standards for design, process, and materials with regards to AM. The committee defined a taxonomy of seven sub-technologies that together constitute the full suite of AM techniques. The seven sub-technologies are described in ASTM F2792-12a, the details of which are hereby incorporated by reference herein.

Material extrusion is an additive manufacturing process where material is selectively dispensed through an extrusion nozzle. The most common implementation of this method involves the extrusion of thermoplastic material through a heated orifice. The materials available for the most common implementation tend to be functional plastics that are sufficiently robust to withstand harsh environments such as chemical, mechanical, or temperature exposure.

Vat photo polymerization features a vat of liquid photo curable polymer that is selectively cured with an energy source such as a laser beam or other optical energy. The part is typically attached to a platform that descends one cure depth after a layer is completed and the process is repeated. This class of additive manufacturing benefits from feature sizes dictated by either the laser beam width or optical resolution in the X and Y axis and minimum cure depth in Z.

Powder bed fusion processes include selectively melting or sintering a layer of powder using an energy source such as a laser or electron beam, lowering the layer by a fabrication layer thickness, and adding a new powder layer by delivery with a rake or roller and material storage mechanism. The process continues with the next layer. Unmelted powder in the bed acts inherently as support material for subsequently built layers.

Material jetting uses ink-jetting or other nozzle-based technology to selectively deposit the build material with a cure prior to the application of subsequent layers. An exemplary version of this technology may be ink-jetting multiple photocurable polymers and follow the inkjet head with a UV lamp for immediate and full volume curing. With multiple materials, fabricated items can be multi-colored or materials can be chosen with varying stiffness properties. Ink-jetting is also naturally well suited for parallelism and thus can be easily scaled to larger and faster production.

Binder jetting includes selectively depositing a binder into a layer of powder feedstock. Additional powder material is then dispensed from a material storage location by a rake or roller mechanism to create the next layer. Some binder jetting technologies may require a post-anneal furnace cycle depending on the materials being used (e.g., metals, ceramics). One exemplary system may inkjet color (much like a commercial inkjet color printer) in addition to the binder into a powder, and may therefore provide structures with colors throughout the structure for conceptual models. Another binder jetting system may utilize a post anneal process to drive out the binder to produce metal or ceramic structures.

Sheet lamination is another additive manufacturing process in which individual sheets of material are bonded together to form three-dimensional objects. In one exemplary embodiment, sheets of metal are bonded together using ultrasonic energy. The process has been shown to produce metallurgical bonds for aluminum, copper, stainless steel, and titanium. A subsequent subtractive process between layers adds internal structures and other complex geometries impossible with conventional subtractive manufacturing processes that start from a billet of material.

Directed energy deposition is another additive manufacturing process that directs both the material deposition and the energy source (typically a laser or electron beam) at the surface being built. Directed energy deposition processes typically use powder or wire-fed metals and exemplary applications of the process may include repair of high value components used in aircraft engines. These directed energy AM processes, as well as the other AM processes described above, can be used to add material to existing parts, components, or devices to provide structurally encoded information. In addition, as the adaptation of AM technologies is advancing to provide end-use products, parts, components, and devices, structural encoding as described herein can be designed within a computer-aided design (CAD) file of a particular part to be fabricated and simultaneously fabricated within or integral with the finished part.

The structurally encoded component of the present disclosure may be manufactured by conventional methods such as a machining operation using any milling, lathe machining, or drilling operation to include standard machining and fabrication methods known in the art of manufacturing structurally encoded components.

The embodiments of FIGS. 1-3 show a structurally encoded component rod structure having a length of one centimeter. Exemplary embodiments of each structurally encoded component shown in FIGS. 1-3 include each notch or material variation having a thickness of 0.1-0.3 millimeters, which results in storage of about 30-40 bits of information on the structurally encoded component rod structure. After utilizing bits for Hamming code error correction, about 25-35 actual data bits create approximately 30 million to 30 billion indexing options into an external database or for limited information stored on the structurally encoded component such as a structurally encoded component expiration date and lot number.

Figure 4:
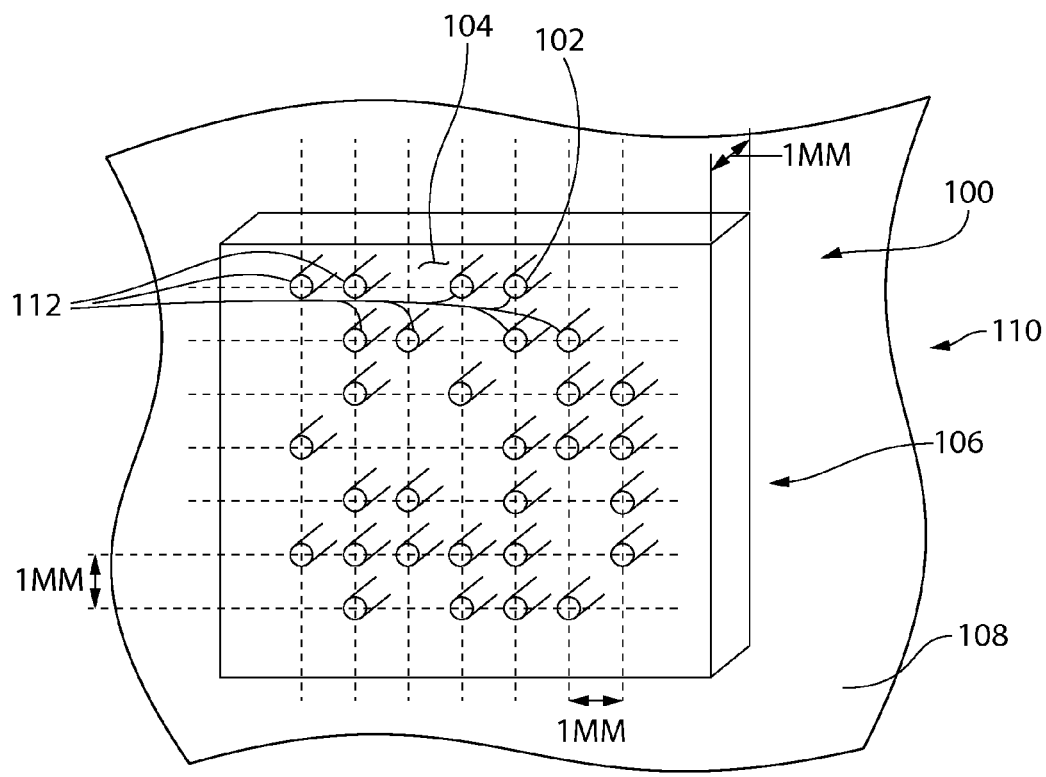
FIG. 4 is a front perspective view of a structurally encoded component in accordance with further aspects of the present disclosure.

Referring now to FIG. 4, a structurally encoded component plate structure 100 of an embodiment of the present disclosure features a two-dimensional array of modifications 102 to a surface 104 of the plate structure 100. The array of modifications 102 of the embodiment of FIG. 4 includes at least two sets of data that can be read from at least two different respective directions, including a first direction disposed at 90 degrees from a second direction. The at least two sets of data may also exist from two different respective perspectives of the array of modifications 102, such as from a read perspective aligned with the Z axis from a first perspective and a read perspective aligned with the X axis from a second perspective. The structurally encoded component plate structure 100 of the embodiment of FIG. 4 features a readable portion 106 shown in FIG. 4 to be integral with an outer structure portion 108 of a structurally encoded component 110. Alternatively, the readable portion 106 of the structurally encoded component 110 may be disposed upon the main portion 108 of the structurally encoded component 110. The readable portion 106 may be coupled to the main portion 108 by such means as fasteners or adhesives or through interference fit. The modifications 102 to the surface 104 of the plate structure 100 shown in FIG. 4 are holes 112 that are micromanufactured through the surface 104 of the plate structure 100. The plate structure 100 may be composed of any material such as a metal, polymer, or ceramic compatible with the imaging modality selected. Further, any single or combination of composite or nanoparticle material, including fine particles between 1 and 100 nanometers in size, may be used for the present structure, such as the readable portion.

The embodiment shown in FIG. 4 features a plate structure 100 that is one centimeter squared and one millimeter thick and has a seven-by-seven array of holes 112. The holes 112 are spaced about one millimeter from each other to provide 49 bits. After subtracting bits used for error correction, approximately four trillion reliable database entry fields with error correction are provided by the seven-by-seven array of holes 112. A Hamming code is implemented in an embodiment of the structurally encoded component with an additional eight bits to provide for the detection and correction of single bit errors.

Figure 5:
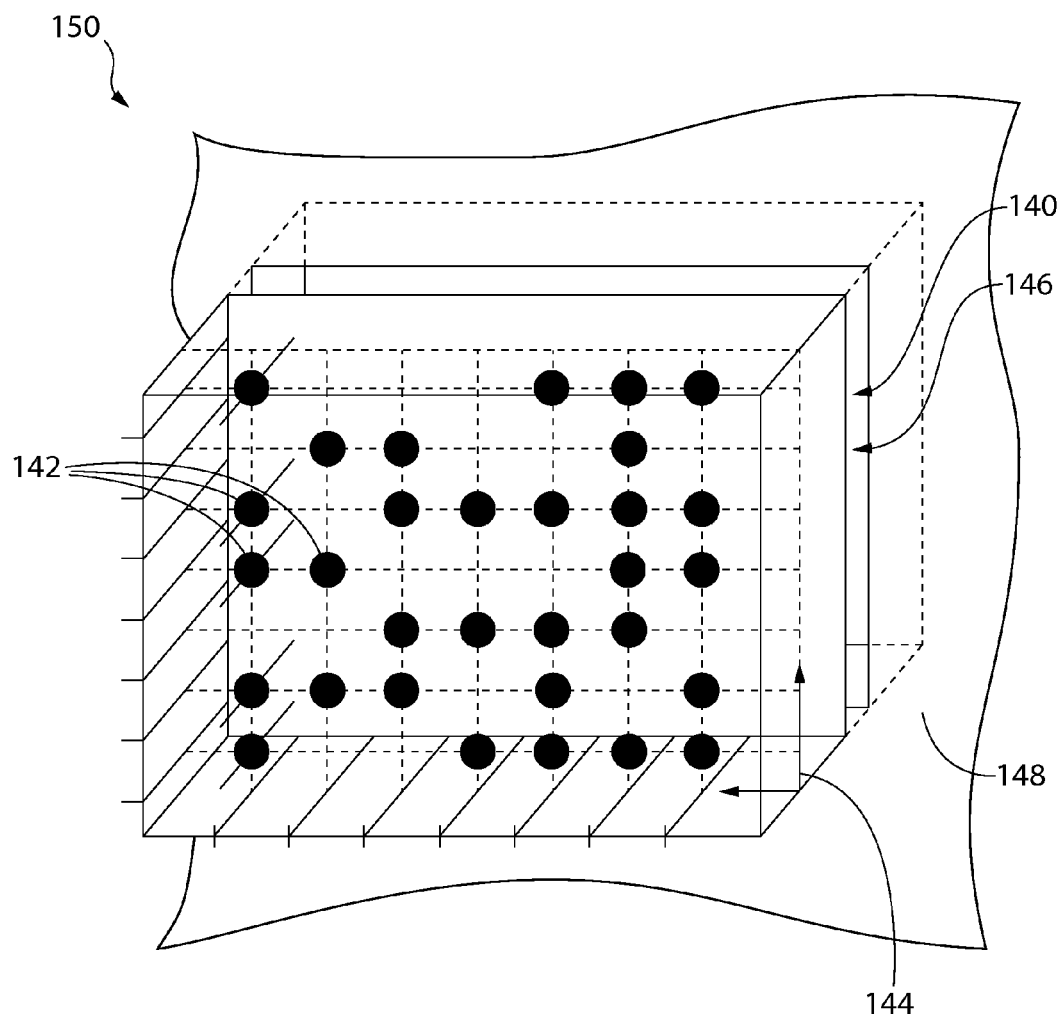
FIG. 5 is a front perspective view of a structurally encoded component in accordance with further aspects of the present disclosure.

Referring now to FIG. 5, a structurally encoded component plate structure 140 of an embodiment of the present disclosure features a two-dimensional array of embedded markers 142 located at an internal plane 144 of the structurally encoded component plate structure 140. The embedded markers 142 of an embodiment are internal volumes of a second material of different density. The structurally encoded component plate structure 140 of FIG. 5 features a readable portion 146 shown in FIG. 5 to be disposed upon an outer structure portion 148 of a structurally encoded component 150. Although not shown in FIG. 5, the readable portion 146 may be coupled to the main portion 148 by such means as fasteners or adhesives or through interference fit. Alternatively, the readable portion 146 of the structurally encoded component 150 may be integral with the main portion 148 of the structurally encoded component 150. The second material having a different density than the plate structure shown in FIG. 5 may be a substance of any material phase including a solid, liquid, or a gas. The embedded markers 142 as an array of internal volumes of FIG. 5 may also be voids in the material of the readable portion 146 of the structurally encoded component plate structure 140. The structurally encoded component plate structure 140 may be composed of any material such as a metal, ceramic, or polymer.

Similar to the plate structure of FIG. 4, the embodiment shown in FIG. 5 features a plate structure 140 that is one centimeter squared and one millimeter thick and has a seven-by-seven array of internal volumes or voids forming embedded markers 142. The markers 142 form an array in an embodiment and include at least two sets of data that can be read from at least two different respective directions, including a first direction disposed at 90 degrees from a second direction. The at least two sets of data may also exist from two different respective perspectives of the array of markers 142, such as from a read perspective aligned with the Z axis from a first perspective and a read perspective aligned with the X axis from a second perspective. The volumes are spaced about one millimeter from each other to provide 49 bits. After subtracting bits used for error correction, four trillion reliable database entry fields with error correction are provided by the seven-by-seven array of volumes or voids. A Hamming code is implemented in an embodiment of the structurally encoded component with an additional eight bits to provide for the detection and correction of single bit errors.

Figure 6:
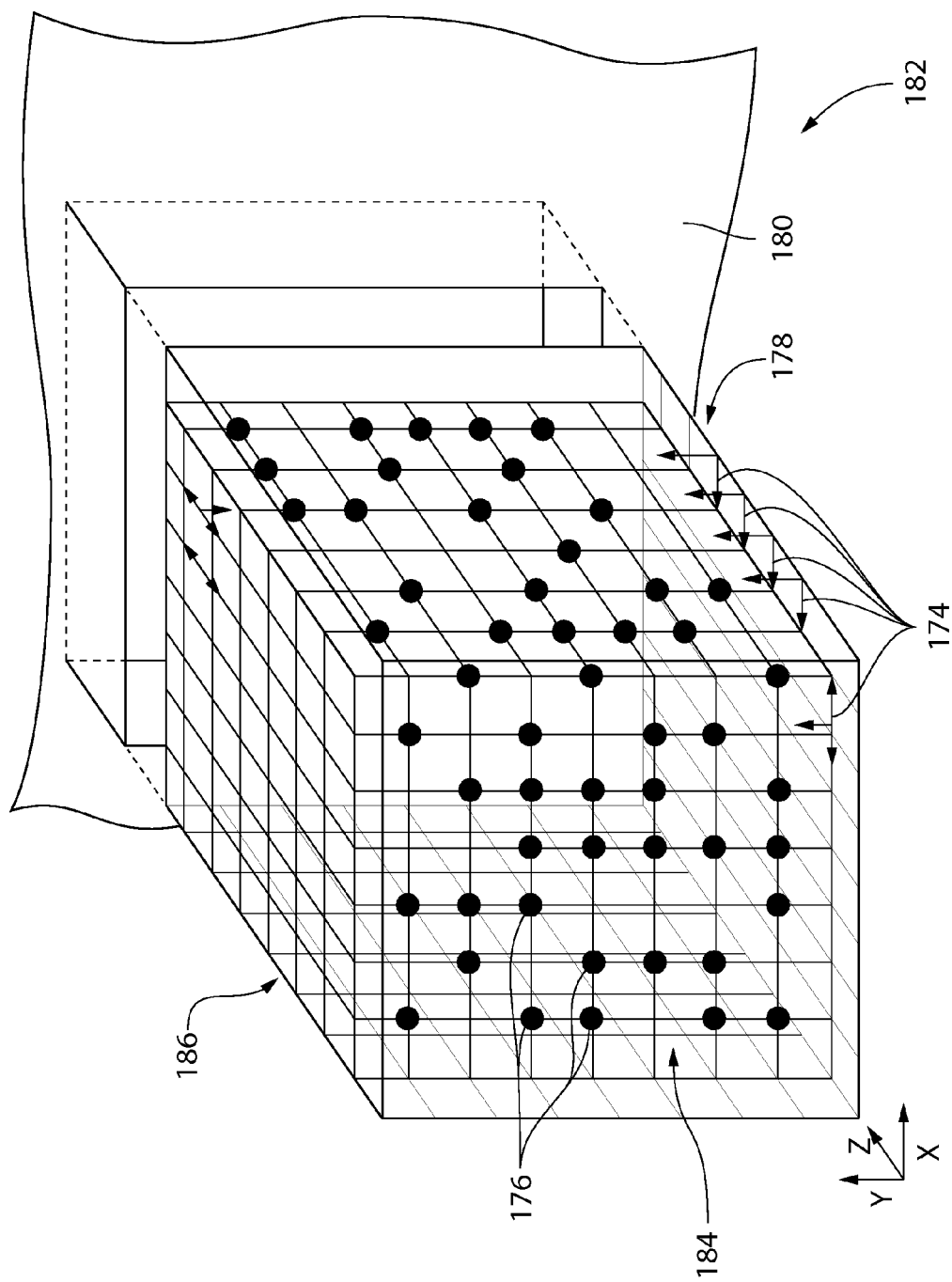
FIG. 6 is a front perspective view of a structurally encoded component in accordance with further aspects of the present disclosure.

Referring now to FIG. 6, a structurally encoded component structure 170 of an embodiment of the present disclosure features a three-dimensional array 186 of embedded markers 176 located on a series of internal planes 174 of the structurally encoded component structure 170 that are separated across the z-axis of the structurally encoded component structure 170. Each of the internal planes 174 shown in FIG. 6 comprise a three-dimensional array of embedded markers 176. The array of markers 176 includes at least three sets of data that can be read from at least three different respective directions, including a first direction disposed at 90 degrees from a second direction along a first plane, and a third direction disposed at 90 degrees from both the first direction and the second direction along a second plane and a third plane. The at least three sets of data may also exist from three different respective perspectives of the array of markers 176, such as from a read perspective aligned with the Z axis from a first perspective, a read perspective aligned with the X axis from a second perspective, and a read perspective aligned with the Y axis from a third perspective. The embedded markers 176 in an embodiment are internal volumes of a second material of differing density than a first material forming the remainder of the structurally encoded component structure 170. The embedded markers 176 may additionally be composed of a material differing from both the first and second materials forming an identifiable structurally encoded component having three or more materials, similar to the structurally encoded component shown in FIG. 3. This material modulation further increases the density of data recorded in the structurally encoded component structure 170.

The structurally encoded component structure 170 of the embodiment of FIG. 6 features a readable portion 178 shown in FIG. 6 to be disposed on an outer structure portion 180 of a structurally encoded component 182. Although not shown in FIG. 6, the readable portion 178 may be coupled to the main portion 180 by such means as fasteners or adhesives or through interference fit. Alternatively, the readable portion 178 of the structurally encoded component 182 may be integral with or within the main portion 180 of the structurally encoded component 182. The second material having a different density than the structurally encoded component structure 170 shown in FIG. 6 may be a substance of any material phase including a solid, liquid, or a gas. The array of internal volumes of FIG. 6 forming embedded markers 176 may also be voids in the material of the readable portion 178 of the structurally encoded component structure 170. The structurally encoded component structure 170 may be composed of any material such as a metal, ceramic, or polymer.

As with the embodiment shown in FIG. 5, each plane 174 in the three-dimensional array 186 of the embodiment shown in FIG. 6 features a unique seven-by-seven two-dimensional array 184 of embedded markers 176. The structurally encoded component structure 170 of FIG. 6 features the seven unique two-dimensional arrays 184 along the planes 174 such that the seven-by-seven-by-seven three-dimensional array 186 is formed. Data is extracted from the three-dimensional array 186 shown in FIG. 6 through volume imaging used with an extraction algorithm and advanced error correction coding in three dimensions. Due to the large amount of data within the internal array 186 of the structurally encoded component structure 170 shown in FIG. 6, external databases may not be required to access detailed structurally encoded component manufacturer, sales, supply chain, engineering drawings and analyses, assembly, material(s), component or assembly history, ownership, or manufacturing process data, or other related records. Through image analysis, a party, such as an owner, service professional, government or industry official, would have immediate access to records encoded entirely within the structurally encoded component 182.

Figure 7:
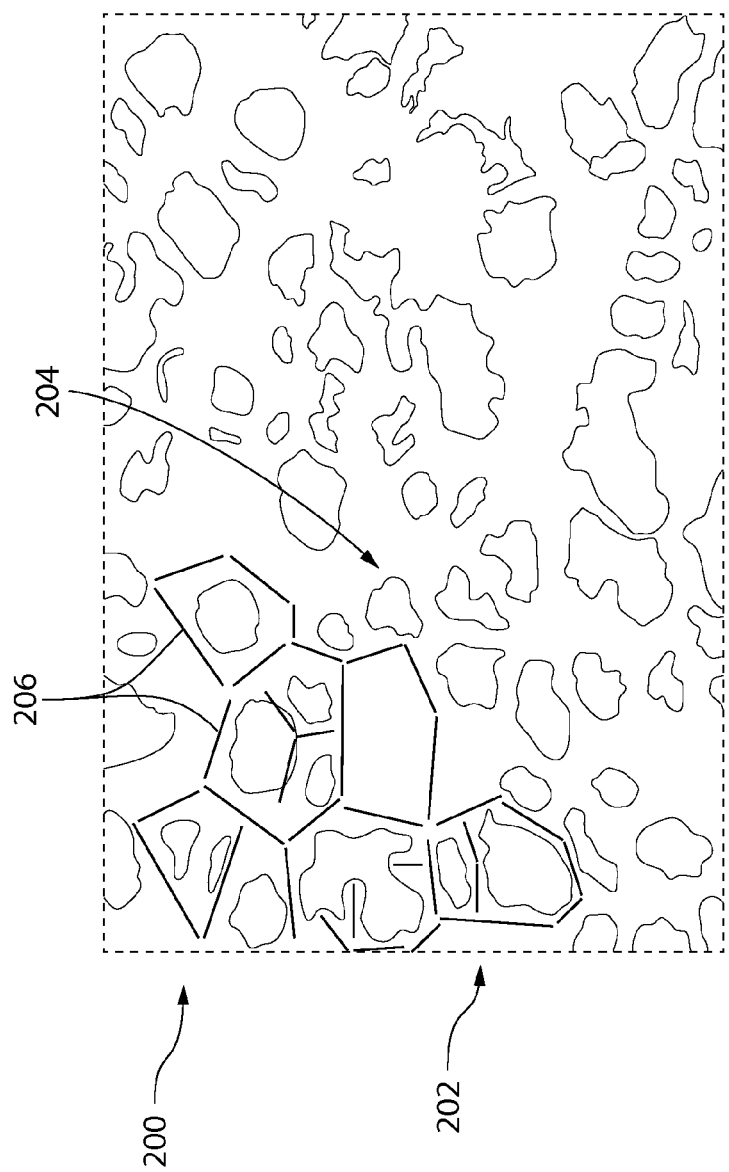
FIG. 7 is an enlarged cross sectional view of a structurally encoded component in accordance with further aspects of the present disclosure.
Figure 8:
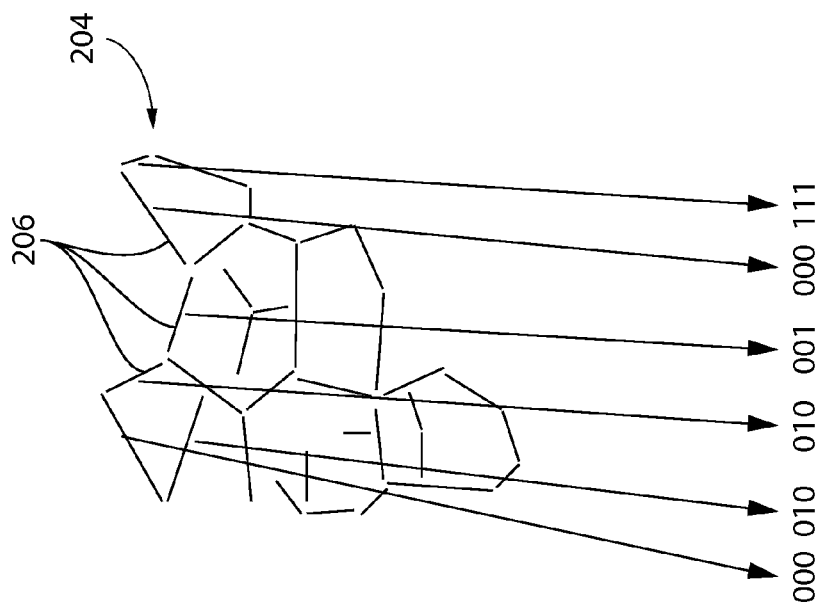
FIG. 8 is a diagram relating to indicia data of a structurally encoded component in accordance with further aspects of the present disclosure.

Reference is now made to FIG. 7, which shows a structurally encoded component structure 200 of an embodiment of the present disclosure. The structurally encoded component structure 200 of an embodiment is a metal mesh structure fabricated using additive manufacturing (also known in the art as 3D printing). The Materials Science & Engineering article titled "Characterization of Ti-6Al-4V Open Cellular Foams Fabricated by Additive Manufacturing Using Electron Beam Melting" by Murr, et al. discusses such additive manufacturing methods to produce such exemplary structures as are displayed in the article, and is hereby incorporated herein by reference. Through an AM manufacturing process, a unique internal structure is formed while maintaining the structural requirements of the structurally encoded component 200. A readable portion 202 includes an internal structure 204 inside the readable portion 202. The internal structure 204 includes linking structures 206 that interconnect to form the internal structure 204. Individual linking structures 206 in the embodiment shown in FIG. 7 each have a predetermined size and orientation in reference to a unique registration structure that would be included in every structurally encoded component and easily identifiable. As shown in FIG. 8, the size and orientation of a particular linking structure 206 of an embodiment of the present disclosure is predetermined to represent binary data. As with the embodiments of the present disclosure shown in FIGS. 1-6, the data is read to gather valuable information relating to the structurally encoded component. The data contained in the readable portion 202 of the structurally encoded component structure 200 can be accurately read through non-invasive or non-destructive means such as x-ray, fluoroscopy, computed tomography, electromagnetic radiation, ultrasound, positron emission tomography, and magnetic resonance imaging. FIGS. 7A and 8A show, in detail, the readable portion 202, internal structure 204, and linking structure 206 of the structurally encoded component structure 200 according to one embodiment of the present disclosure. If, for example, the component structure 200 is load bearing, the linking structures 206 is capable of maintaining the desired and/or necessary mechanical properties for static or dynamic performance of the component structure 200.

One or more of the embodiments of the present disclosure are structurally encoded components, which refers to the 3D encoding of digital information in a structure as variations in geometric or physical features—widths, densities, color, feature angles, etc. Bar codes are an example of a 2D encoding of digital information with modulations of color (dark versus light) with varying widths of printed bars on a surface. A typical embodiment of the structurally encoded components of the present disclosure may contain data that is not readily apparent to a viewer of the device structure. Further, encoding of the typical embodiments of the present disclosure is handled by physical means other than those accomplished through circuitry, electromagnetic or other, within the structurally encoded component itself or through a type of internal storage means such as magnetic storage means or the like. Such structurally encoded components, as disclosed herein and described in relation to the typical and/or potential embodiments of the present disclosure allow simplified production, maintenance, and/or operation costs for identification, storage, and/or retrieval of unique structurally encoded component data while retaining a substantial amount of information with reduced probability for error.

Figure 10:
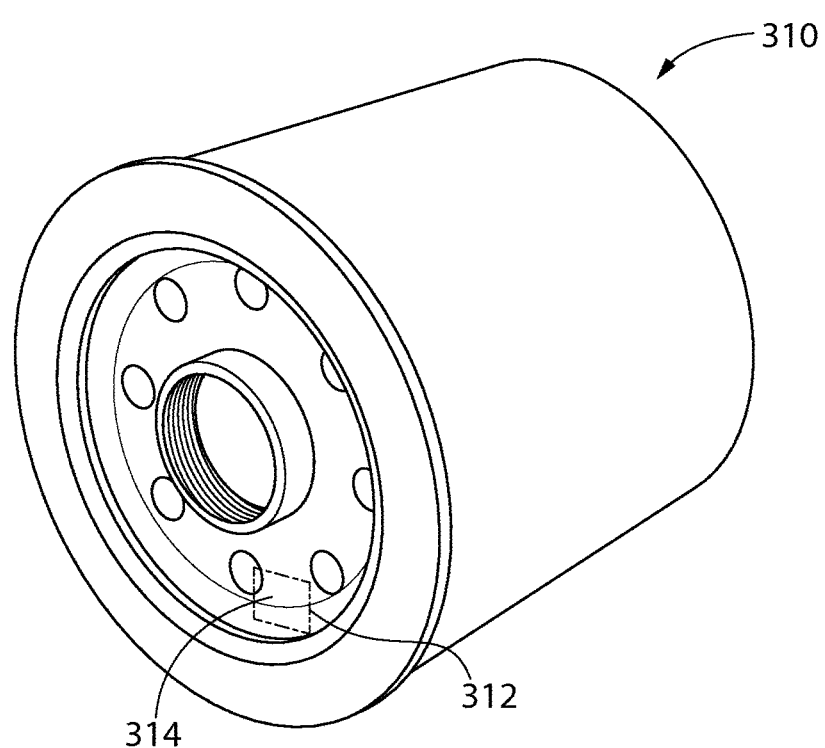
FIG. 10 is a perspective view of a structurally encoded component in accordance with further aspects of the present disclosure.

Referring now to FIGS. 10-14, the structurally encoded component of the present disclosure is shown in several embodiments. Referring specifically to FIG. 10, a structurally encoded vehicle part 310 is shown. The vehicle part 310 of the embodiment shown in FIG. 10 is an oil filter, which is a replaceable part in a vehicle's engine assembly. At an internal location 312 of the vehicle part 310, a readable portion 314 is structurally encoded with data that may be related to the filter manufacturer, the filter serial number, the vehicle type or model for which the filter is designed, the manufacture or installation date, or any recall or manufacture service information. The readable portion 314 may be structured or manufactured according to any of the embodiments discussed above or shown in FIGS. 1-9. Such encoded information may be read via any of the imaging methods discussed above, including x-ray, fluoroscopy, computed tomography, electromagnetic radiation, ultrasound, positron emission tomography, and magnetic resonance imaging, and may include error correction as discussed above. Other parts contemplated by the present disclosure may include one or more fasteners, such as the machine screw shown in FIG. 9, utilized in a vehicle or other assembly and encoded with data relating to the part or assembly. One example of the structurally encoded vehicle part includes a structurally encoded section of a vehicle engine block constructed using laser engineered net shaping (LENS), an additive manufacturing directed energy deposition technology, onto the existing engine block structure manufactured by another method, such as traditional casting, forging, and machining. The methods described above may be used to provide structural encoding on virtually any automotive part by (1) directly fabricating components with structural encoding either externally accessible or fully embedded within the component and not accessible without one or more of the imaging processes described herein, or (2) fabricating a fraction or portion of a major component or subsystem with structural encoding information on or in it, and then incorporating the portion on or in the major component either as an attachment or embedded within a larger component through assembly or integration during fabrication of the larger component.

Figure 11:
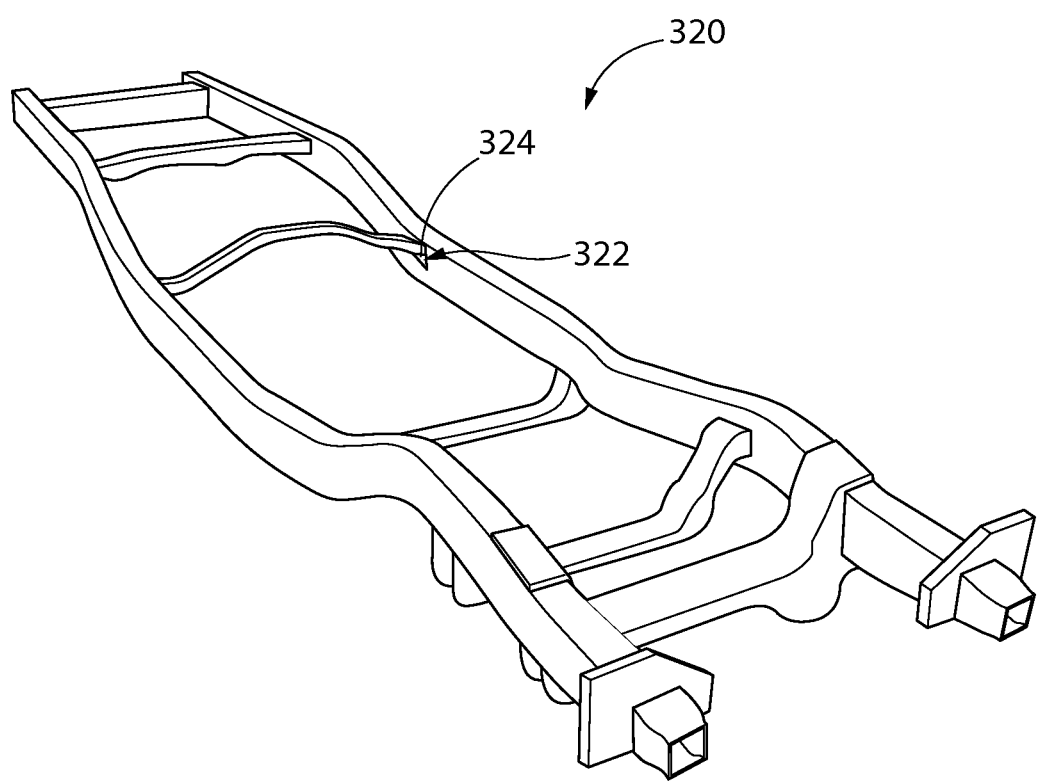
FIG. 11 is a perspective view of a structurally encoded component in accordance with further aspects of the present disclosure.

Referring now to FIG. 11, a structurally encoded vehicle frame 320 is shown to include a structurally encoded component 322. It is contemplated that the structurally encoded vehicle frame 320 of the present disclosure may include a passenger car or truck frame, a motorcycle frame, a watercraft hull, an aircraft or spacecraft frame, or any military or law enforcement vehicle, aircraft, spacecraft, or watercraft. The structurally encoded component 322 of the vehicle frame 320 of the embodiment shown in FIG. 11 is a frame gusset that is welded onto the remaining frame portions to create the unitary frame. The structurally encoded component 322 may include a separate readable portion 324 or the component 322 may itself be the readable portion 324. The readable portion 324 is structurally encoded with data that may be related, as non-limiting examples, to the vehicle manufacturer, the vehicle identification number (VIN) or serial number, the vehicle type, model, engineering drawings or analyses, or production number, the manufacture, assembly, or sale date, any recall, service, repair, or ownership information.

Further, any of the embodiments of the present disclosure may include data relating to the unique image, properties, or manufacturing characteristics of the part or component itself, such as particular programming language directed to identification or replication of the structure.

In the embodiment shown in FIG. 11, the structurally encoded component 322 provides a redundant means of identifying the vehicle. In the event that a vehicle identification number displayed at other vehicle locations, such as displayed on a dashboard plate, a frame plate, or stamped onto the frame or engine, is altered, replaced, or removed, the vehicle identification number contained in the data of the readable portion 324 of the structurally encoded component 322 provides a secure means of retaining data pertaining to the vehicle with the vehicle. The structurally encoded component 322 may also take the form of another vehicle component such as a dashboard part, a vehicle panel, a wheel component, or an engine component.

The readable portion 324 may be structured or manufactured according to any of the embodiments discussed above or shown in FIGS. 1-9. Such encoded information may be read via any of the imaging methods discussed above, including x-ray, fluoroscopy, computed tomography, electromagnetic radiation, ultrasound, positron emission tomography, and magnetic resonance imaging, and may include error correction as discussed above.

Figure 12:
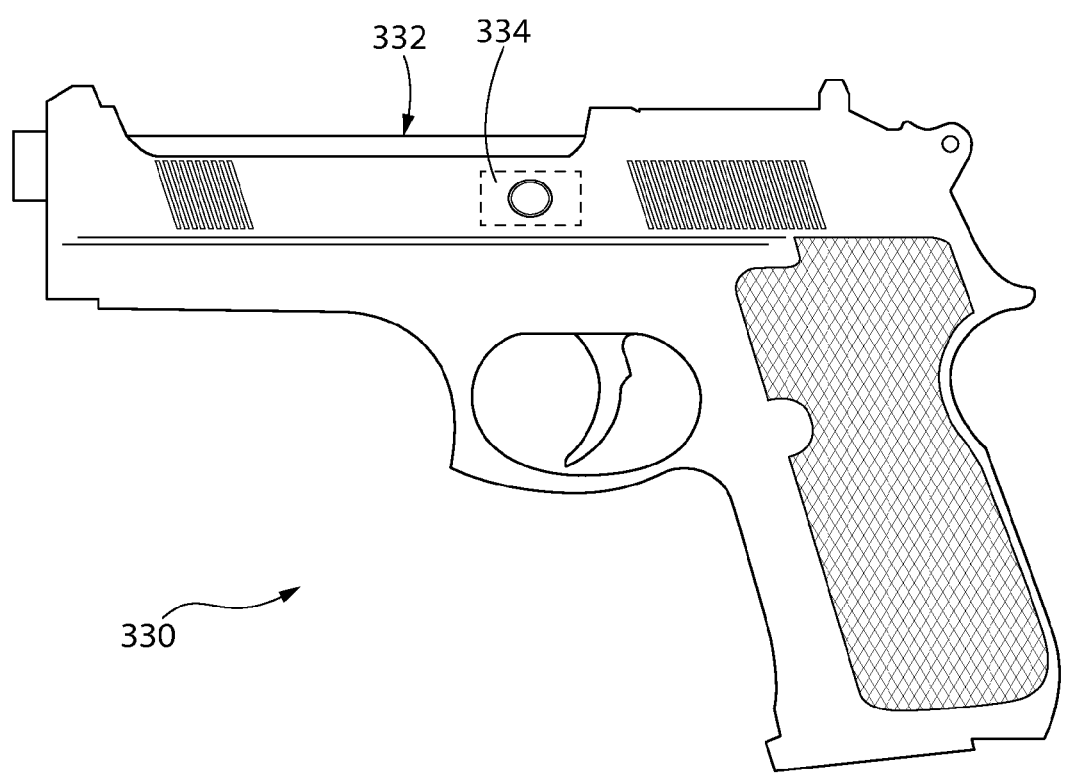
FIG. 12 is a perspective view of a structurally encoded component in accordance with further aspects of the present disclosure.

Referring now to FIG. 12, a weapon 330 having a structurally encoded component 332 is shown. The weapon 330 shown in FIG. 12 is a firearm, but any weapon, such as a knife or other bladed weapon or a projectile launching weapon, is contemplated by the present disclosure. The structurally encoded component 332 is or includes a readable portion 334, which is a barrel portion of the weapon 330. However, the readable portion 334 may be located elsewhere, such as a stock or grip of a firearm. As firearms and other weapons are sensitive objects that are tracked by government and law enforcement agencies, an embedded or otherwise secure readable portion 334 prevents illicit purchasing, trafficking, or carrying of weapons, while also preventing alteration or removal of serial numbers located on weapons such as firearms. The methods described above may be used to provide structural encoding on virtually any weapon or weapon part by (1) directly fabricating components with structural encoding either externally accessible or fully embedded within the component and not accessible without one or more of the imaging processes described herein, or (2) fabricating a fraction or portion of a major component or subsystem with structural encoding information on or in it, and then incorporating the portion on or in the major component either as an attachment or embedded within a larger component through assembly or integration during fabrication of the larger component.

The readable portion 334 is structurally encoded with data that may be related to the weapon manufacturer, the serial number, the weapon type, model, engineering design drawings and analyses, or production number, ammunition, the manufacture, assembly, or sale date, and any recall, service, repair, or ownership information, including country of origin. The readable portion 334 may be structured or manufactured according to any of the embodiments discussed above or shown in FIGS. 1-9. Such encoded information may be read via any of the imaging methods discussed above, including x-ray, fluoroscopy, computed tomography, electromagnetic radiation, ultrasound, positron emission tomography, and magnetic resonance imaging, and may include error correction as discussed above.

Figure 13:
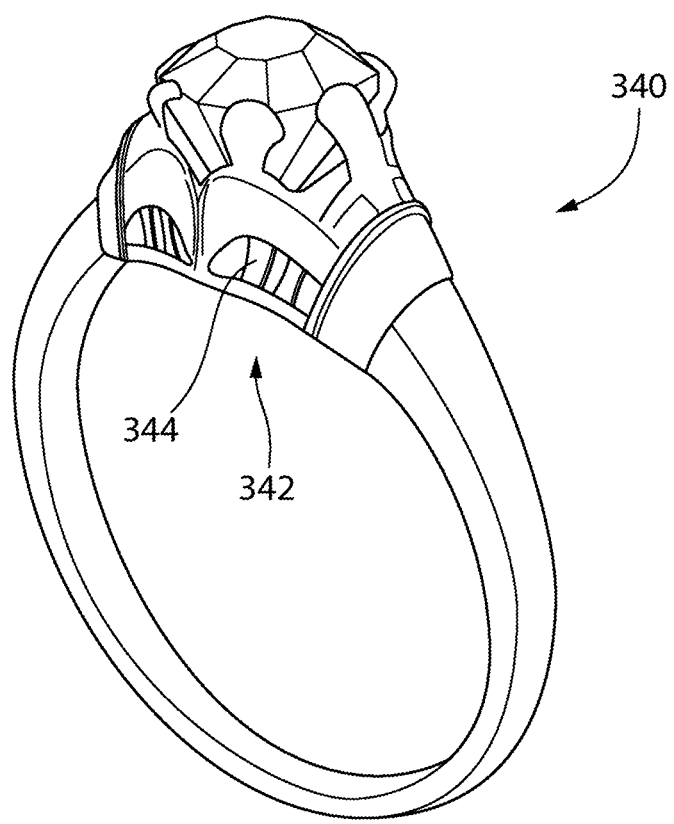
FIG. 13 is a perspective view of a structurally encoded component in accordance with further aspects of the present disclosure.

Referring now to FIG. 13, a piece of jewelry 340 having a structurally encoded component 342 is shown. The jewelry 340 shown in FIG. 13 is a ring having a precious metal base with one or more gemstones embedded within. However, any type of jewelry, such as bracelets, necklaces, watches, or earrings, is contemplated by the present disclosure. Additionally, the structurally encoded component 342 is, or forms part of, an in-ear hearing aid or other personalized medical instrument. The structurally encoded component 342 is or includes a readable portion 344. The readable portion 344, as shown in FIG. 13, is located integrally at an inner portion of the ring, but may be separately attachable as a decorative and/or valuable component to the jewelry. The readable portion 344 allows an enhanced measure of security for the jewelry as the methods for encoding discussed above allow a large amount of data to be included in a very small space, such as a surface or inner space of a piece of jewelry.

The readable portion 344 of the jewelry shown in FIG. 13 is structurally encoded with data that may be related to the jewelry designer, the design information including dates, the material type and quality, the serial number, any gemstone information such as research or laboratory certification or grading, history, any sale, repair, or evaluation date, insurance information, and any ownership information. Because many valuable gemstones, such as diamonds, include a serial number engraved onto their surface, the structurally encoded component 342 of the present disclosure provides secure confirmation of such data for a piece of jewelry that includes the valuable gemstone.

The readable portion 344 may be structured or manufactured according to any of the embodiments discussed above or shown in FIGS. 1-9. Such encoded information may be read via any of the imaging methods discussed above, including x-ray, fluoroscopy, computed tomography, electromagnetic radiation, ultrasound, positron emission tomography, and magnetic resonance imaging, and may include error correction as discussed above.

As further contemplated by the present disclosure, other sensitive objects, such as pharmaceutical goods, having structurally encoded components, packaging, or containers would benefit from the efficient and secure identification, tracking, and storage of information relating to the objects. Additionally, the structurally encoded components discussed herein may be incorporated into or form part of consumer electronics such as cell phones, or toys to track information relating to such products.

The embodiments of the present disclosure, as shown individually in FIGS. 1-13, may be manufactured by one or more of the AM processes described above. The method of manufacturing an identifiable structurally encoded component according to an embodiment of the present disclosure comprises providing an outer structure portion of an identifiable structurally encoded component, providing a readable portion of an identifiable structurally encoded component, printing a first material onto a first readable portion surface to create a first printed layer, and printing the first material onto the first printed layer to create a second printed layer. At least one of the printing of the first material onto the first readable portion surface and the printing of the first material onto the first printed layer comprises printing encoded indicia. Further, the encoded indicia may comprise volumes of a second material having a different density than the first material found elsewhere in the readable portion of the identifiable structurally encoded component. As an example, the readable portion of an identifiable structurally encoded component may be formed by an additive manufacturing (AM) or 3D printing process such that micro-volumes of a metal material having a relatively high density are deposited within a polymer substrate having a relatively low density. The encoded indicia may also comprise voids in the first material of the identifiable structurally encoded component. Further, any single embodiment of the present disclosure may be manufactured using a combination of traditional manufacturing processes and additive manufacturing processes. For example, a 3D printed structurally encoded component with internal indicia formed by the 3D printing process may also have a series of notches micromachined onto an exterior surface of the 3D printed structurally encoded component.

The identifiable structurally encoded component of the present disclosure enables more accurate reporting, reviewing, and analyzing of adverse event reports so that problem devices can be identified and corrected more quickly. Additionally, the identifiable structurally encoded component of the present disclosure reduces error by manufacturing professionals, service professionals, and others to rapidly and precisely identify a device and obtain important information concerning the characteristics of the device. The present disclosure enhances analysis of devices on the market by providing a standard and clear way to document device use in electronic records, testing information systems, claim data sources, and registries. Through the structurally encoded component of the present disclosure, a more robust postmarket surveillance system may also be leveraged to support premarket approval or clearance of new devices and new uses of currently marketed devices. The present disclosure further provides a standardized identifier that will allow manufacturers, distributors, and service facilities to more effectively manage device recalls. Moreover, the present disclosure provides a foundation for a global, secure distribution chain, helping to address theft, counterfeiting, and diversion and prepare for emergencies. The identifiable structurally encoded component of the present disclosure enables development of a device identification system that is recognized around the world.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

I claim:

1. A structurally encoded component storing identification data, said structurally encoded component comprising:
   a readable body defining a plurality of planes, wherein each of said planes comprises separately readable indicia such that said indicia are discernible by at least one of x-ray, fluoroscopy, computed tomography, electromagnetic radiation, ultrasound, positron emission tomography, and magnetic resonance imaging, wherein said indicia comprise at least two sets of data that can be read from at least two different respective directions with respect to said readable body, and wherein each of said planes comprising said separately readable indicia is subsurface of the structurally encoded component.

2. The structurally encoded component of claim 1, further comprising an outer structure portion of said structurally encoded component and a readable portion of said structurally encoded component, wherein said readable portion comprises said readable body and is integral with said outer structure portion.

3. The structurally encoded component of claim 1, further comprising an outer structure portion of said structurally encoded component and a readable portion of said structurally encoded component, wherein said readable portion comprises said readable body and is disposed upon said outer structure portion.

4. The structurally encoded component of claim 1, wherein said at least two different respective directions includes a first direction disposed at 90 degrees from a second direction.

5. The structurally encoded component of claim 1, wherein said indicia comprises information in the form of a code.

6. The structurally encoded component of claim 5, wherein said code comprises an error correction code.

7. The structurally encoded component of claim 5, wherein said code comprises a Hamming code.

8. The structurally encoded component of claim 1, wherein said separately readable indicia are not readily apparent to a viewer of the structurally encoded component.

9. A structurally encoded component storing identification data, said structurally encoded component comprising:
   a readable body defining a plurality of linking structures, each of said linking structures having at least one of a predetermined size and orientation, said linking structures being interconnected to substantially form said readable body, and said linking structures forming predetermined indicia such that said indicia are discernible by at least one of x-ray, fluoroscopy, computed tomography, electromagnetic radiation, ultrasound, positron emission tomography, and magnetic resonance imaging, and wherein said predetermined indicia are subsurface of the structurally encoded component.

10. The structurally encoded component of claim 9, further comprising an outer structure portion of said structurally encoded component and a readable portion of said structurally encoded component, wherein said readable portion comprises said readable body and is integral with said outer structure portion.

11. The structurally encoded component of claim 9, further comprising an outer structure portion of said structurally encoded component and a readable portion of said structurally encoded component, wherein said readable portion comprises said readable body and is disposed upon said outer structure portion.

12. The structurally encoded component of claim 9, wherein said indicia in said structurally encoded component comprise an error correction or detection code.

13. The structurally encoded component of claim 9, wherein said predetermined indicia are not readily apparent to a viewer of the structurally encoded component.

14. A structurally encoded component storing identification data, said structurally encoded component comprising:
   a readable body comprising at least one detectable element and indicia as a plurality of detectable elements disposed within said structurally encoded component such that said indicia are discernible by at least one of x-ray, fluoroscopy, computed tomography, electromagnetic radiation, ultrasound, positron emission tomography, and magnetic resonance imaging, and wherein said plurality of detectable elements is subsurface of the structurally encoded component.

15. The structurally encoded component of claim 14, further comprising an outer structure portion of said structurally encoded component and a readable portion of said structurally encoded component, wherein said readable portion comprises said readable body and is integral with said outer structure portion.

16. The structurally encoded component of claim 14, further comprising an outer structure portion of said structurally encoded component and a readable portion of said structurally encoded component, wherein said readable portion comprises said readable body and is disposed upon said outer structure portion.

17. The structurally encoded component of claim 14, wherein said plurality of detectable elements includes an array of voids in said readable portion.

18. The structurally encoded component of claim 17, wherein said array of voids in said readable portion forms at least one bar code.

19. The structurally encoded component of claim 18, wherein said at least one bar code comprises an error correction code.

20. The structurally encoded component of claim 18, wherein said at least one bar code comprises a Hamming code.

21. The structurally encoded component of claim 14, wherein said plurality of detectable elements are not readily apparent to a viewer of the structurally encoded component.

22. A method of manufacturing a structurally encoded component, comprising:
   printing a first material onto a first surface to create a first printed layer,
   printing said first material onto said first printed layer to create a second printed layer, wherein at least one of said printing said first material onto said first surface and said printing said first material onto said first printed layer comprises printing encoded indicia, and wherein said encoded indicia are subsurface of the structurally encoded component.

23. The method of claim 22, wherein said encoded indicia comprise voids in said first material.

24. The method of claim 22, further comprising:
printing a second material onto at least one of said first surface and said first printed layer, such that said encoded indicia comprises said second material.

25. The method of claim 22, wherein said encoded indicia are discernible by at least one of x-ray, fluoroscopy, computed tomography, electromagnetic radiation, ultrasound, positron emission tomography, and magnetic resonance imaging.

26. The method of claim 22, wherein said encoded indicia contain unique data referencing additional information located in an external database.

27. The method of claim 22, wherein said encoded indicia comprise information in the form of a code.

28. The method of claim 27, wherein said code comprises code having at least one of error detection and correction.

29. The method of claim 27, wherein said code comprises data compression code.

30. The method of claim 22, wherein said structurally encoded component comprises a second material different from said first material.

31. The method of claim 22, wherein said encoded indicia are not readily apparent to a viewer of the structurally encoded component.

32. A method of manufacturing a structurally encoded component, comprising:
printing a first material onto a first surface to create a first printed layer,
printing a second material onto said first printed layer to create a second printed layer, wherein at least one of said printing said first material onto said first surface and said printing said second material onto said first printed layer comprises printing encoded indicia, and wherein said encoded indicia are subsurface of the structurally encoded component.

33. The method of claim 32, wherein said encoded indicia comprise voids in at least one of said first material and said second material.

34. The method of claim 32, wherein said encoded indicia are discernible by at least one of x-ray, fluoroscopy, computed tomography, electromagnetic radiation, ultrasound, positron emission tomography, and magnetic resonance imaging.

35. The method of claim 32, wherein said encoded indicia contain unique data referencing additional information located in an external database.

36. The method of claim 32, wherein said encoded indicia are not readily apparent to a viewer of the structurally encoded component.

* * * * *